(12) United States Patent
Lee et al.

(10) Patent No.: US 8,182,979 B2
(45) Date of Patent: May 22, 2012

(54) PHOTOPOLYMERIZATION INITIATOR CONTAINING UNSATURATED DOUBLE BOND AND OXIME ESTER GROUP AND PHOTOSENSITIVE RESIN COMPOSITION COMPRISING THE SAME

(75) Inventors: Keon Woo Lee, Daejeon (KR); Raisa Kharbash, Daejeon (KR); Chang Ho Cho, Anseong-si (KR); Sung Hyun Kim, Daejeon (KR); Sang Kyu Kwak, Daejeon (KR); Dong Kung Oh, Daejeon (KR); Chang Soon Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 411 days.

(21) Appl. No.: 12/588,886

(22) Filed: Oct. 30, 2009

(65) Prior Publication Data
US 2010/0112479 A1    May 6, 2010

(30) Foreign Application Priority Data
Nov. 5, 2008   (KR) .................. 10-2008-0109200

(51) Int. Cl.
*C07D 209/82* (2006.01)
*C08F 2/48* (2006.01)
*G03F 7/028* (2006.01)
*G03F 7/033* (2006.01)

(52) U.S. Cl. ............... 430/284.1; 430/285.1; 430/286.1; 430/287.1; 430/288.1; 430/920; 430/919; 522/63; 548/440

(58) Field of Classification Search .................. None
See application file for complete search history.

(56) References Cited

FOREIGN PATENT DOCUMENTS
JP    2004-359639 A  * 12/2004
WO   WO 02100903 A1 * 12/2002

OTHER PUBLICATIONS

English translation of JP, 2004-359639 , A (2004) from machine translation from AIPN Japan Patent Office National Center for Industrial Property Information and Training, generated Feb. 10, 2012, 15 pages.*
Anonymously, "use of ketoxime-esters", Research Disclosure Database No. 437035, published Sep. 2000, 5 pages.*

* cited by examiner

*Primary Examiner* — Cynthia Hamilton
(74) *Attorney, Agent, or Firm* — McKenna Long & Aldridge LLP

(57) ABSTRACT

A photopolymerization initiator is provided. The photopolymerization initiator contains at least one unsaturated double bond and at least one oxime ester group in the molecule. The photopolymerization initiator comprises a compound represented by Formula 1 or 2:

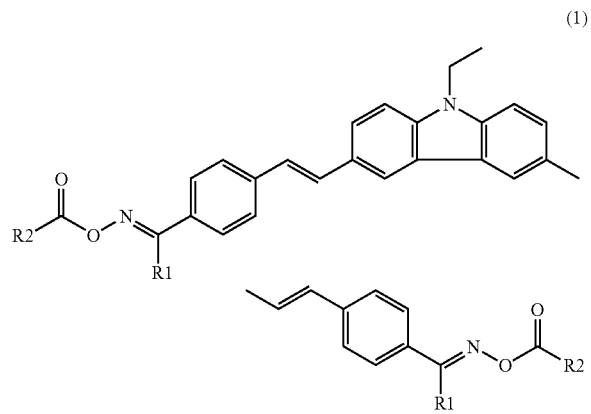

(1)

wherein R1 and R2 are each independently —$CH_3$, —$C_2H_5$, —$C_3H_7$ or —$C_6H_5$;

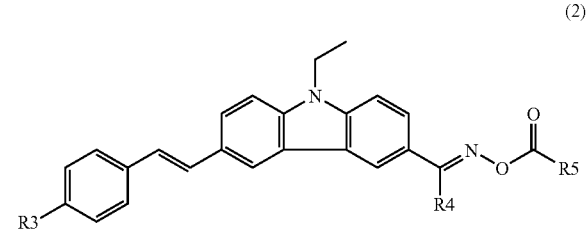

(2)

wherein R3, R4 and R5 are each independently —$CH_3$, —$C_2H_5$, —$C_3H_7$ or —$C_6H_5$.

Further provided is a photosensitive resin composition comprising the photopolymerization initiator. The use of the photosensitive resin composition in photolithography reduces the formation of volatile residue during post-development baking.

8 Claims, 1 Drawing Sheet

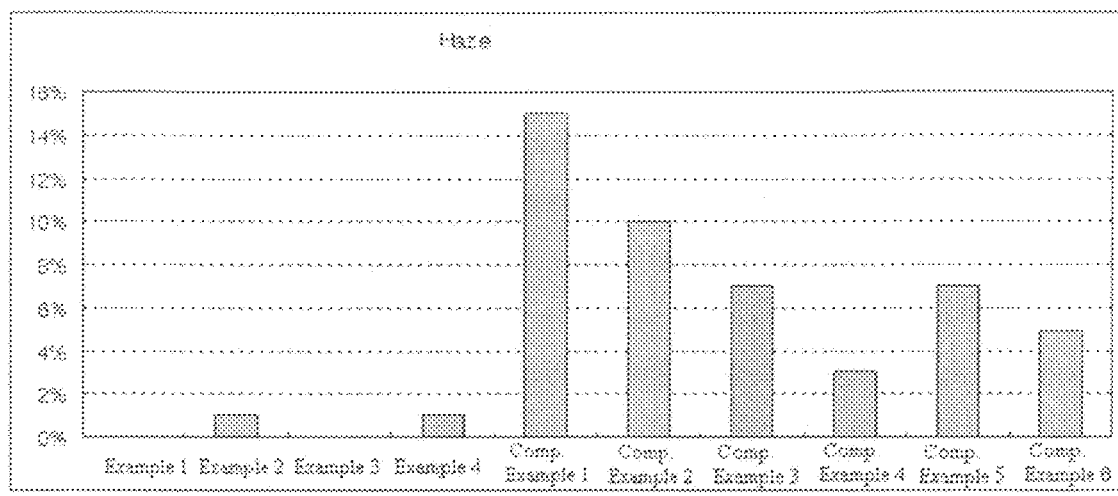

PHOTOPOLYMERIZATION INITIATOR CONTAINING UNSATURATED DOUBLE BOND AND OXIME ESTER GROUP AND PHOTOSENSITIVE RESIN COMPOSITION COMPRISING THE SAME

BACKGROUND OF THE INVENTION

1. Field of the Invention

The present invention relates to an initiator of a photosensitive resin composition for use in photolithography, and more specifically to a photopolymerization initiator containing at least one unsaturated double bond and at least one oxime ester group in the molecule.

2. Description of the Related Art

Photolithograpy is the most widely used method for fabricating liquid crystal display devices and semiconductor devices. A photosensitive composition for use in photolithography is essentially composed of a photoreaction initiator that tends to generate radicals due to its sensitivity to UV light, a crosslinkable compound containing two or more unsaturated double bonds, a polymeric binder that can be developed by an alkaline aqueous solution to form a thin film, a solvent, and one or more additives. A general photolithography process involves the following steps: washing of a glass or silicon substrate; application of a photosensitive material in the form of a solution; vacuum drying and drying prior to exposure for the removal of the solvent; UV exposure through a photomask in an exposure system to form a pattern; removal the unexposed portion using a solution based on an alkaline aqueous solution to form a thin film; and post-development baking at high temperature to improve the heat resistance and durability of the thin film. Of these steps, the exposure step may also be carried out by direct laser scanning or digital exposure using a micromirror or a microlens, instead of the use of the photomask.

Residue remains after every step of the photolithography process to deteriorate the performance of the equipment and to promote the aging of the equipment, thus causing inconvenience that the production lines of the equipment need to be stopped for periodic washing. Particularly, when the thin film is processed at a temperature as high as 180° C. in the post-development baking step, various kinds of volatile substances are adhered to the inner walls of the equipment. Generally, the solvent in the form of a liquid tends to evaporate continuously with the passage of time, leaving no residue behind. There is little possibility that the additives used in very small amounts may leave residue. However, the photopolymerization initiator in the form of a solid is vaporized together with the solvent and is again solidified on the inner walls of the equipment, leaving residue in the form of a gel or powder. The solid residue falls on the substrate in the subsequent steps to cause defects of final devices.

In recent years, attempts to increase the sensitivity of photosensitive materials have been made to achieve improved productivity in the fabrication of devices using photolithography. An increase in the content of a photopolymerization initiator sensitive to UV light in a photosensitive resin composition is considered as the easiest way. However, inevitable residue from the photopolymerization initiator makes the fabrication of the devices difficult to manage, which becomes an obstacle to the improvement of productivity.

Thus, there is a need for a photopolymerization initiator that is not readily vaporized in the post-development baking step, leaving little residue.

SUMMARY OF THE INVENTION

It is an object of the present invention to provide a photopolymerization initiator that leaves no residue after post-development baking.

It is another object of the present invention to provide a photosensitive resin composition comprising the photopolymerization initiator.

According to an aspect of the present invention, there is provided a photopolymerization initiator represented by Formula 1 or 2:

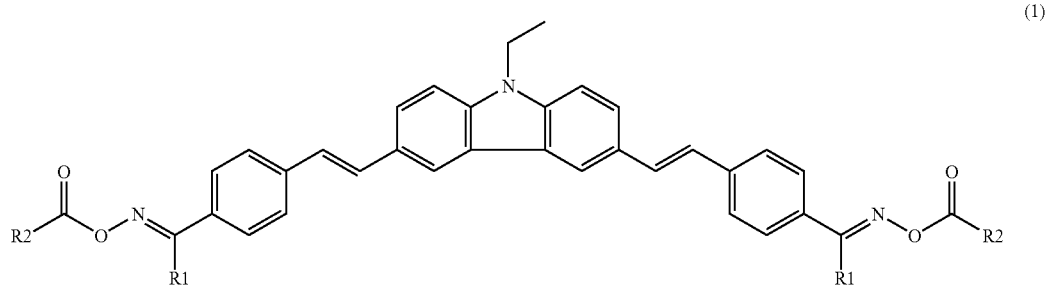

(1)

wherein R1 and R2 are each independently —$CH_3$, —$C_2H_5$, —$C_3H_7$ or —$C_6H_5$;

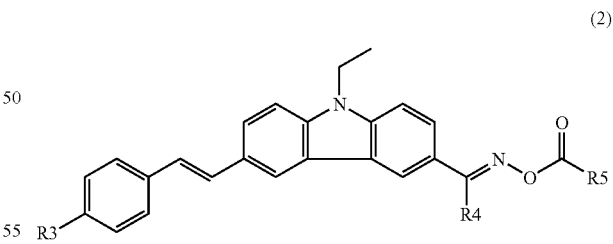

(2)

wherein R3, R4 and R5 are each independently —$CH_3$, —$C_2H_5$, —$C_3H_7$ or —$C_6H_5$.

According to another aspect of the present invention, there is provided a photosensitive resin composition comprising (A) an alkali-soluble resin binder, (B) a crosslinkable compound containing two or more unsaturated acrylic bonds, (C) a photopolymerization initiator, and (D) a solvent wherein the photopolymerization initiator (C) comprises either a compound represented by Formula 1:

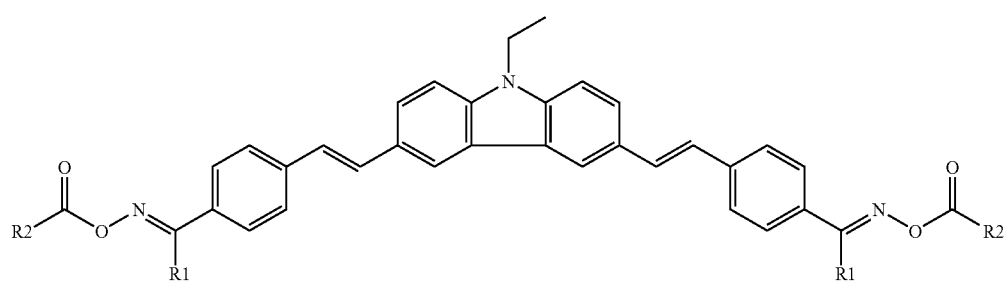

(1)

wherein R1 and R2 are each independently —CH₃, —C₂H₅, —C₃H₇ or —C₆H₅; or
a compound represented by Formula 2:

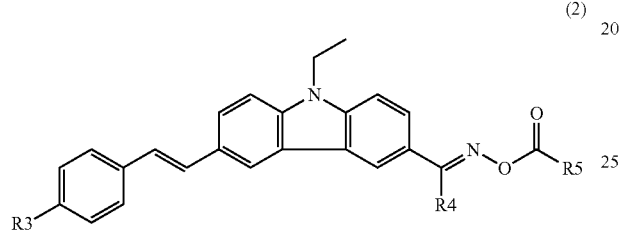

(2)

wherein R3, R4 and R5 are each independently —CH₃, —C₂H₅, —C₃H₇ or —C₆H₅; both of the compounds of Formulas 1 and 2.

The photosensitive resin composition of the present invention may further comprise at least one additive selected from colorants, curing accelerators, surfactants, solvents, adhesion promoters, and other additives, depending on the intended applications.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 1 is a graph showing the haze values of thin films formed using photosensitive resin compositions of Examples 1-4 and Comparative Examples 1-6.

DETAILED DESCRIPTION OF THE INVENTION

The present invention provides a photopolymerization initiator represented by Formula 1 or 2:

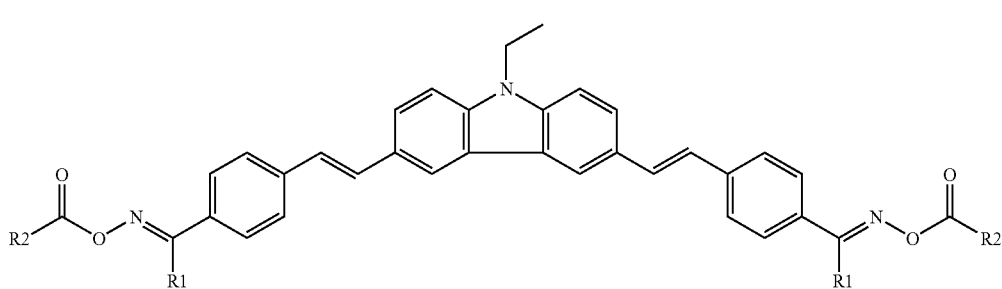

(1)

wherein R1 and R2 are each independently —CH₃, —C₂H₅, —C₃H₇ or —C₆H₅;

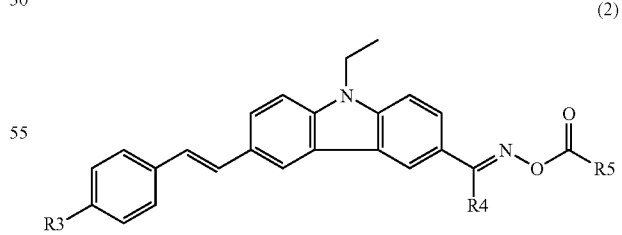

(2)

wherein R3, R4 and R5 are each independently —CH₃, —C₂H₅, —C₃H₇ or —C₆H₅.

The present invention also provides a photosensitive resin composition comprising (A) an alkali-soluble resin binder, (B) a crosslinkable compound containing two or more unsaturated acrylic bonds, (C) a photopolymerization initiator, and (D) a solvent wherein the photopolymerization initiator (C) comprises either a compound represented by Formula 1:

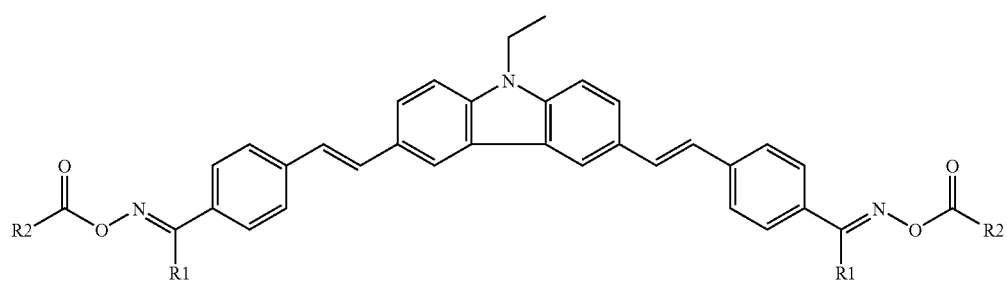

(1)

wherein R1 and R2 are each independently —CH₃, —C₂H₅, —C₃H₇ or —C₆H₅; or
a compound represented by Formula 2:

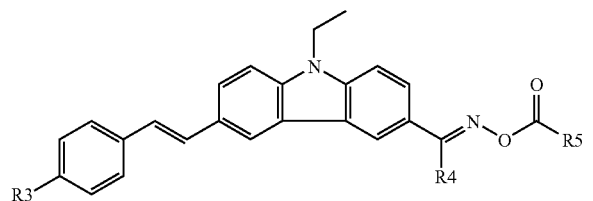

(2)

wherein R3, R4 and R5 are each independently —CH₃, —C₂H₅, —C₃H₇ or —C₆H₅; or both of the compounds of Formulas 1 and 2.

The photopolymerization initiator (C) may be a mixture of the compound of Formula 1 or 2 and one or more other photopolymerization initiators so long as the effects of the present invention are not sacrificed. That is, the photopolymerization initiator (C) is not necessarily composed of only the compound of Formula 1 or 2.

Examples of such additional photopolymerization initiators include triazine compounds, such as 2,4-trichloromethyl-(4'-methoxyphenyl)-6-triazine, 2,4-trichloromethyl-(4'-methoxystyryl)-6-triazine, 2,4-trichloromethyl-(piperonyl)-6-triazine, 2,4-trichloromethyl-(3',4'-dimethoxyphenyl)-6-triazine, 3-{4-[2,4-bis(trichloromethyl)-s-triazin-6-yl]phenylthio}propanoic acid, 2,4-trichloromethyl-(4'-ethylbiphenyl)-6-triazine and 2,4-trichloromethyl-(4'-methylbiphenyl)-6-triazine; biimidazole compounds, such as 2,2'-bis(2-chlorophenyl)-4,4',5,5'-tetraphenylbiimidazole and 2,2'-bis(2,3-dichlorophenyl)-4,4',5,5'-tetraphenylbiimidazole; acetophenone compounds, such as 2-hydroxy-2-methyl-1-phenylpropan-1-one, 1-(4-isopropylphenyl)-2-hydroxy-2-methylpropan-1-one, 4-(2-hydroxyethoxy)-phenyl (2-hydroxy)propyl ketone, 1-hydroxycyclohexyl phenyl ketone, 2,2-dimethoxy-2-phenyl acetophenone, 2-methyl-(4-methylthiophenyl)-2-morpholino-1-propan-1-one (Irgacure-907) and 2-benzyl-2-dimethylamino-1-(4-morpholinophenyl)-butan-1-one (Irgacure-369); O-acyloxime compounds, such as Irgacure OXE 01 and Irgacure OXE 02, both of which are commercially available from Ciba Geigy; benzophenone compounds, such as 4,4'-bis(dimethylamino)benzophenone and 4,4'-bis(diethylamino)benzophenone; thioxanthone compounds, such as 2,4-diethyl thioxanthone, 2-chlorothioxanthone, isopropylthioxanthone and diisopropylthioxanthone; phosphine oxide compounds, such as 2,4,6-trimethylbenzoyldiphenylphosphine oxide, bis(2,6-dimethoxybenzoyl)-2,4,4-trimethylpentylphosphine oxide and bis(2,6-dichlorobenzoyl)propylphosphine oxide; and coumarin compounds, such as 3,3'-carbonylvinyl-7-(diethylamino)coumarin, 3-(2-benzothiazolyl)-7-(diethylamino) coumarin, 3-benzoyl-7-(diethylamino)coumarin, 3-benzoyl-7-methoxy-coumarin and 10,10'-carbonylbis[1,1,7,7-tetramethyl-2,3,6,7-tetrahydro-1H,5H,11H-Cl]-benzopyrano[6,7,8-ij]-quinolizin-11-one.

The alkali-soluble resin binder (A) does not require any particular structure so long as it can be developed to form a thin film due to the presence of organic acid groups in the molecule. For example, the alkali-soluble resin binder (A) may be a polymer having a molecular weight of 20,000 that is prepared by radical polymerization of benzyl methacrylate and methacrylic acid in a molar ratio of 7:3. There is no particular limitation on the molecular weight and the preparation method of the alkali-soluble resin binder (A).

The crosslinkable compound (B) may be mixed with at least one crosslinkable compound containing two or more unsaturated acrylic bonds. Any known crosslinkable compound may be mixed with the crosslinkable compound (B), and examples thereof include: compounds prepared by esterifying at least one polyhydric alcohol selected from ethylene glycol di(meth)acrylate, polyethylene glycol di(meth)acrylate having 2 to 14 ethylene groups, trimethylolpropane di(meth)acrylate, trimethylolpropane tri(meth)acrylate, pentaerythritol tri(meth)acrylate, pentaerythritol tetra(meth)acrylate, 2-trisacryloyloxymethylethylphthalic acid, propylene glycol di(meth)acrylate having 2 to 14 propylene groups, dipentaerythritol penta(meth)acrylate, dipentaerythritol hexa(meth)acrylate and mixtures (TO-2348 and TO-2349, Toagosei Co., Ltd., Japan) of an acid-modified product of dipentaerythritol penta(meth)acrylate and dipentaerythritol hexa(meth)acrylate, with an α,β-unsaturated carboxylic acid; compounds prepared by adding (meth)acrylic acid to at least one glycidyl group-containing compound selected from trimethylolpropane triglycidyl ether acrylic acid adducts and bisphenol A diglycidyl ether acrylic acid adducts; and adducts of at least one compound having a hydroxyl group or an ethylenically unsaturated bond selected from phthalic acid diester of β-hydroxyethyl(meth)acrylate and toluene diisocyanate adducts of β-hydroxyethyl(meth)acrylate, and at least one ester selected from ester compounds of polyvalent carboxylic acids and polyisocyanate. If needed, a silica dispersion may be added to the crosslinkable compounds to improve the mechanical strength of a final thin film. Commercially available silica dispersions are Nanocryl XP series 0596, 1045 and 21/1364 and Nanopox XP series 0516 and 0525, all of which are sold by Hanse Chemie GmbH.

Optionally, the photosensitive resin composition of the present invention may further comprise at least one additive selected from colorants, curing accelerators, thermal polymerization inhibitors, plasticizers, surfactants, solvents, adhesion promoters and fillers.

The colorants may be pigments, dyes and mixtures thereof. As black pigments, there may be exemplified carbon black, graphite and metal oxides (e.g., titanium black). Commercially available carbon black products are, for example: SEAST 5HIISAF-HS, SEAST KH, SEAST 3HHAF-HS, SEAST NH, SEAST 3M, SEAST 300HAF-LS, SEAST 116HMMAF-HS, SEAST 116MAF, SEASTF MFEF-HS, SEAST SOFEF, SEAST VGPF, SEAST SVHSRF-HS and SEAST SSRF, all of which are sold by Tokai Carbon Co., Ltd.; DIAGRAM BLACK II, DIAGRAM BLACK N339, DIAGRAM BLACK SH, DIAGRAM BLACK H, DIAGRAM LH, DIAGRAM HA, DIAGRAM SF, DIAGRAM N550M, DIAGRAM M, DIAGRAM E, DIAGRAM G, DIAGRAM R, DIAGRAM N760M, DIAGRAM LR, #2700, #2600, #2400, #2350, #2300, #2200, #1000, #980, #900, MCF88, #52, #50, #47, #45, #45L, #25, #CF9, #95, #3030, #3050, MA7, MA77, MA8, MA11, MA100, MA40, OIL7B, OIL9B, OIL11B, OIL30B and OIL31B, all of which are sold by Mitsubishi Chemical Corp.; PRINTEX-U, PRINTEX-V, PRINTEX-140U, PRINTEX-140V, PRINTEX-95, PRINTEX-85, PRINTEX-75, PRINTEX-55, PRINTEX-45, PRINTEX-300, PRINTEX-35, PRINTEX-25, PRINTEX-200, PRINTEX-40, PRINTEX-30, PRINTEX-3, PRINTEX-A, SPECIAL BLACK-550, SPECIAL BLACK-350, SPECIAL BLACK-250, SPECIAL BLACK-100 and LAMP BLACK-101, all of which are sold by Degussa; and RAVEN-1100ULTRA, RAVEN-1080ULTRA, RAVEN-1060ULTRA, RAVEN-1040, RAVEN-1035, RAVEN-1020, RAVEN-1000, RAVEN-890H, RAVEN-890, RAVEN-880ULTRA, RAVEN-860ULTRA, RAVEN-850, RAVEN-820, RAVEN-790ULTRA, RAVEN-780ULTRA, RAVEN-760ULTRA, RAVEN-520, RAVEN-500, RAVEN-460, RAVEN-450, RAVEN-430ULTRA, RAVEN-420, RAVEN-410, RAVEN-2500ULTRA, RAVEN-2000, RAVEN-1500, RAVEN-1255, RAVEN-1250, RAVEN-1200, RAVEN-1190ULTRA and RAVEN-1170, all of which are sold by Colombia Carbon Co. These carbon black products may be used alone or as a mixture thereof. Examples of colorants that can produce colors include: Carmine 6B (C.I.12490); Phthalocyanine Green (C.I. 74260); Phthalocyanine Blue (C.I. 74160); Perylene Black (BASF K0084 and K0086); Cyanine Black; Lionol Yellow (C.I.21090); Lionol Yellow GRO (C.I. 21090); Benzidine Yellow 4T-564D; Victoria Pure Blue (C.I.42595); C.I. PIGMENT RED 3, 23, 97, 108, 122, 139, 140, 141, 142, 143, 144, 149, 166, 168, 175, 177, 180, 185, 189, 190, 192, 202, 214, 215, 220, 221, 224, 230, 235, 242, 254, 255, 260, 262, 264 and 272; C.I. PIGMENT GREEN 7 and 36; C.I. PIGMENT BLUE 15:1, 15:3, 15:4, 15:6, 16, 22, 28, 36, 60 and 64; C.I. PIGMENT YELLOW 13, 14, 35, 53, 83, 93, 95, 110, 120, 138, 139, 150, 151, 154, 175, 180, 181, 185, 194 and 213; and C.I. PIGMENT VIOLET 15, 19, 23, 29, 32 and 37. White pigments and fluorescent pigments may also be used. The phthalocyanine complexes may be those that contain zinc as the metal center in addition to copper.

The curing accelerators may be those known in the art, and examples thereof include 2-mercaptobenzoimidazole, 2-mercaptobenzothiazole, 2-mercaptobenzooxazole, 2,5-dimercapto-1,3,4-thiadiazole, 2-mercapto-4,6-dimethylaminopyridine, pentaerythritol tetrakis(3-mercaptopropionate), pentaerythritol tris(3-mercaptopropionate), pentaerythritol tetrakis(2-mercaptoacetate), pentaerythritol tris(2-mercaptoacetate), trimethylolpropane tris(2-mercaptoacetate), trimethylolpropane tris(3-mercaptopropionate), trimethylolethane tris(2-mercaptoacetate), and trimethylolethane tris(3-mercaptopropionate). These curing accelerators may be used alone or as a mixture of two or more thereof.

The thermal polymerization inhibitors may be those known in the art. Examples of suitable thermal polymerization inhibitors p-anisole, hydroquinone, pyrocatechol, t-butylcatechol, N-nitrosophenylhydroxyamine ammonium salt, N-nitrosophenylhydroxyamine aluminum salt and phenothiazine. These thermal polymerization inhibitors may be used alone or as a mixture of two or more thereof.

The plasticizers, adhesion promoters, fillers and surfactants may be those used in conventional photosensitive resin compositions.

The solvent (D) may be selected from the group consisting of, but not limited to, methyl ethyl ketone, methyl cellosolve, ethyl cellosolve, ethylene glycol dimethyl ether, ethylene glycol diethyl ether, propylene glycol dimethyl ether, propylene glycol diethyl ether, diethylene glycol dimethyl ether, diethylene glycol diethyl ether, diethylene glycol methyl ethyl ether, 2-ethoxy propanol, 2-methoxy propanol, 3-methoxy butanol, cyclohexanone, cyclopentanone, propylene glycol methyl ether acetate, propylene glycol ethyl ether acetate, 3-methoxybutyl acetate, ethyl 3-ethoxypropionate, ethyl cellosolve acetate, methyl cellosolve acetate, butyl acetate, dipropylene glycol monomethyl ether, and mixtures thereof.

The photosensitive resin composition of the present invention is transparent and can be applied to a suitable support such as a metal, paper, glass or plastic substrate by any suitable process such as roll coating, curtain coating, spin coating, slot die coating, printing or dipping. After the photosensitive resin composition is applied to a support (e.g., a film), the coating can be transferred to another support. There is no particular restriction on the application method of the photosensitive resin composition.

The photosensitive resin composition of the present invention can be cured under a suitable light source, for example, a mercury vapor, carbon or xenon (Xe) arc that emits light having a wavelength of 250 to 450 nm.

The alkali-soluble resin binder (A), the crosslinkable compound (B) and the photopolymerization initiator (C) are preferably used in amounts of 1 to 20% by weight, 1 to 30% by weight and 0.1 to 5% by weight, respectively, based on the total weight of the photosensitive resin composition. It is preferred to limit the content of the photopolymerization initiator (C), which may be the compound of Formula 1 or 2 or a mixture thereof with one or more other photopolymerization initiators, below 5% by weight, based on the total weight of the photosensitive resin composition. The solvent may be used in an amount of 10 to 95% by weight, based on the total weight of the photosensitive resin composition. The photosensitive resin composition of the present invention preferably comprises 0.5 to 20% by weight of a colorant and 0.01 to 5% by weight of other additives, based on the total weight of the composition.

The photosensitive resin composition of the present invention can be used in various applications, preferably pigment-dispersion type photoresists for the production of thin film transistor-liquid crystal display (TFT-LCD) color filters, photoresists for the formation of black matrixes of TFT-LCDs or organic light emitting diodes, photoresists for the formation of overcoat layers, and photoresists for the formation of column spacers. The photosensitive resin composition of the present invention can also be used in photocurable paints, photocurable inks, photocurable adhesives, printed boards, photoresists for printed wiring boards, other transparent photoresists, etc. Further, the photosensitive resin composition of the present invention can be used in the manufacture of PDPs.

Hereinafter, the present invention will be explained in more detail with reference to the following examples, including synthesis examples. However, these examples are given for illustrative purposes only and are not intended to limit the present invention.

EXAMPLES

Example 1

8 wt % of benzyl methacrylate/methacrylic acid (molar ratio: 7/3, Mw: 24,000) as an alkali-soluble resin binder, 8 wt % of dipentaerythritol hexaacrylate as a crosslinkable compound containing two or more unsaturated acrylic bonds, 2 wt % of the compound of Formula 1 (R1, R2=$CH_3$) as a photopolymerization initiator, and 82 wt % of PGMEA as a solvent were mixed in a shaker for 3 hr. The mixture was filtered through a 5 micron filter to obtain a photosensitive resin composition.

The photosensitive resin composition was applied to a glass substrate (8 cm (w)×8 cm (l)) by spin coating, slit coating, dip coating or doctor blading to form a uniform thin film. The thin film was prebaked at 100° C. for 200 sec to remove the solvent. After the prebaking, the thin film had a thickness of about 10 mm. The thin film was exposed to a high-pressure mercury lamp with an exposure energy of 100 mJ/$cm^2$ through a photomask, developed with an aqueous 0.04% KOH solution at 23° C. using a sprayer, washed with deionized water, and dried using high-pressure dry air.

The resulting thin film was placed on a hot plate set at 200° C., and a transparent glass substrate was positioned about 1 cm above the thin film. After one hour, the haze of the overlying glass substrate was measured.

Example 2

A photosensitive resin composition was prepared in the same manner as in Example 1, except that the compound of Formula 2 (R3, R4, R5=—$CH_3$) was used instead of the compound of Formula 1 (R1, R2=$CH_3$). A thin film was formed using the photosensitive resin composition in accordance with the procedure described in Example 1. The haze of the thin film was measured.

Example 3

A photosensitive resin composition was prepared in the same manner as in Example 1, except that the compound of Formula 1 (R1=phenyl (—$C_6H_5$), R2=—$CH_3$) was used instead of the compound of Formula 1 (R1, R2=$CH_3$). A thin film was formed using the photosensitive resin composition in accordance with the procedure described in Example 1. The haze of the thin film was measured.

Example 4

A photosensitive resin composition was prepared in the same manner as in Example 1, except that the compound of Formula 2 (R4=phenyl (—$C_6H_5$), R3, R5=—$CH_3$) was used instead of the compound of Formula 1 (R1, R2=$CH_3$). A thin film was formed using the photosensitive resin composition in accordance with the procedure described in Example 1. The haze of the thin film was measured.

Comparative Example 1

A photosensitive resin composition was prepared in the same manner as in Example 1, except that Irgacure 907 (Ciba Geigy) was used instead of the compound of Formula 1 (R1, R2=$CH_3$). A thin film was formed using the photosensitive resin composition in accordance with the procedure described in Example 1. The haze of the thin film was measured.

Comparative Example 2

A photosensitive resin composition was prepared in the same manner as in Example 1, except that Irgacure 369 (Ciba Geigy) was used instead of the compound of Formula 1 (R1, R2=$CH_3$). A thin film was formed using the photosensitive resin composition in accordance with the procedure described in Example 1. The haze of the thin film was measured.

Comparative Example 3

A photosensitive resin composition was prepared in the same manner as in Example 1, except that Irgacure OXE-01 (Ciba Geigy) was used instead of the compound of Formula 1 (R1, R2=$CH_3$). A thin film was formed using the photosensitive resin composition in accordance with the procedure described in Example 1. The haze of the thin film was measured.

Comparative Example 4

A photosensitive resin composition was prepared in the same manner as in Example 1, except that Irgacure OXE-02 (Ciba Geigy) was used instead of the compound of Formula 1 (R1, R2=$CH_3$). A thin film was formed using the photosensitive resin composition in accordance with the procedure described in Example 1. The haze of the thin film was measured.

Comparative Example 5

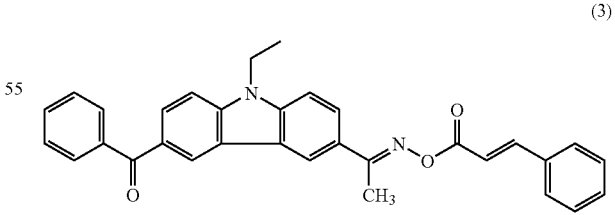

(3)

A photosensitive resin composition was prepared in the same manner as in Example 1, except that the compound of Formula 3 was used instead of the compound of Formula 1 (R1, R2=$CH_3$). A thin film was formed using the photosensitive resin composition in accordance with the procedure described in Example 1. The haze of the thin film was measured.

Comparative Example 6

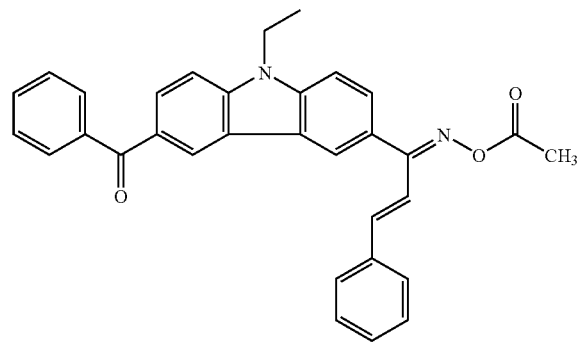

A photosensitive resin composition was prepared in the same manner as in Example 1, except that the compound of Formula 4 was used instead of the compound of Formula 1 (R1, R2=CH$_3$). A thin film was formed using the photosensitive resin composition in accordance with the procedure described in Example 1. The haze of the thin film was measured.

The haze values of the thin films formed in Examples 1-4 and Comparative Examples 1-6 are shown in Table 1 and FIG. 1.

TABLE 1

| Sample | Haze (%) |
|---|---|
| Example 1 | 0 |
| Example 2 | 1 |
| Example 3 | 0 |
| Example 4 | 1 |
| Comparative Example 1 | 15 |
| Comparative Example 2 | 10 |
| Comparative Example 3 | 7 |
| Comparative Example 4 | 3 |
| Comparative Example 5 | 7 |
| Comparative Example 6 | 5 |

Like the photopolymerization initiators used in Examples 1-4, each of the compounds of Formulas 3 and 4 used in Comparative Examples 5 and 6 contains an unsaturated double bond. However, unlike the photosensitive resin compositions of Examples 1-4, the photosensitive resin compositions of Comparative Examples 5 and 6 did not exhibit the desired effects because the unsaturated double bonds adjacent to the respective oxime ester groups were readily cleaved.

From these results, it can be concluded that the use of the compositions of Examples 1-4 in photolithography reduces the formation of volatile residue during post-development baking.

As is apparent from the above description, the use of the photosensitive resin composition according to the present invention in the fabrication of devices by photolithography reduces the formation of residue during drying prior to exposure or post-development baking, making it easy to manage the fabrication of the devices.

What is claimed is:
1. A photopolymerization initiator represented by Formula 1 or 2:

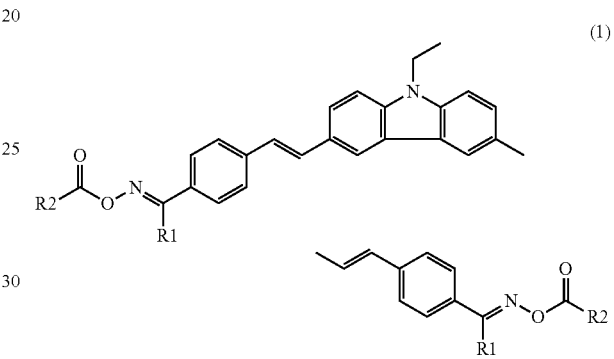

wherein R1 and R2 are each independently —CH$_3$, —C$_2$H$_5$, —C$_3$H$_7$ or —C$_6$H$_5$;

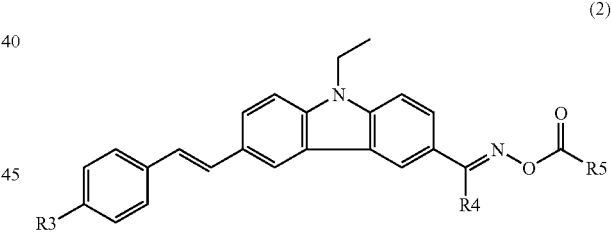

wherein R3, R4 and R5 are each independently —CH$_3$, —C$_2$H$_5$, —C$_3$H$_7$ or —C$_6$H$_5$.

2. A photopolymerization initiator comprising either a compound represented by Formula 1:

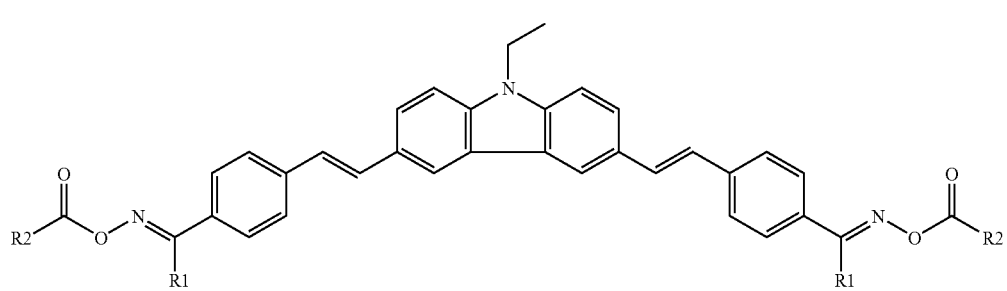

wherein R1 and R2 are each independently —CH$_3$, —C$_2$H$_5$, —C$_3$H$_7$ or —C$_6$H$_5$; or a compound represented by Formula 2:

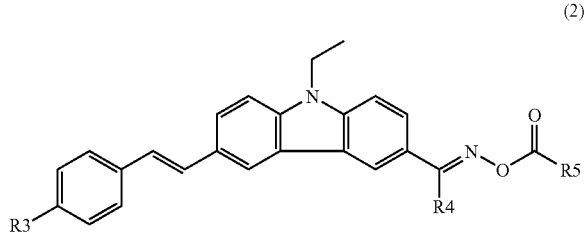

(2)

wherein R3, R4 and R5 are each independently —CH$_3$, —C$_2$H$_5$, —C$_3$H$_7$ or —C$_6$H$_5$; or both of the compounds of Formulas 1 and 2.

3. A photosensitive resin composition comprising (A) an alkali-soluble resin binder, (B) a crosslinkable compound containing two or more unsaturated acrylic bonds, (C) a photopolymerization initiator, and (D) a solvent wherein the photopolymerization initiator (C) comprises either a compound represented by Formula 1:

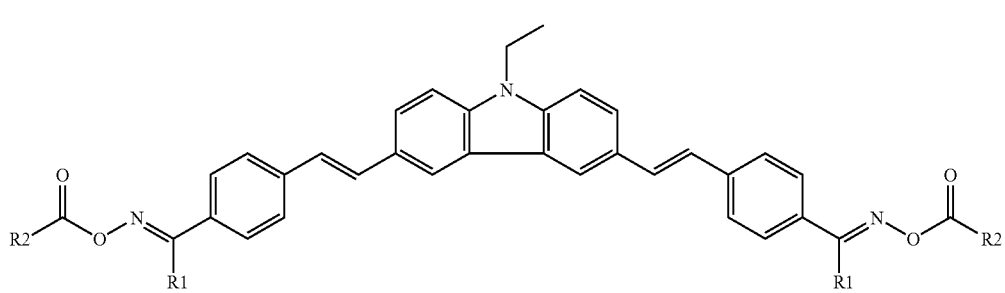

(1)

wherein R1 and R2 are each independently —CH$_3$, —C$_2$H$_5$, —C$_3$H$_7$ or —C$_6$H$_5$; or a compound represented by Formula 2:

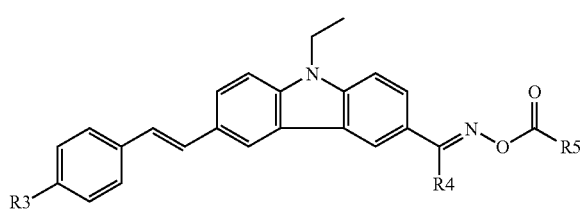

(2)

wherein R3, R4 and R5 are each independently —CH$_3$, —C$_2$H$_5$, —C$_3$H$_7$ or —C$_6$H$_5$; or both of the compounds of Formulas 1 and 2.

4. The photosensitive resin composition of claim 3, wherein the composition comprises 1 to 20% by weight of the alkali-soluble resin binder (A), 1 to 30% by weight of the crosslinkable compound (B), 0.1 to 5% by weight of the photopolymerization initiator (C), with the balance of the organic solvent (D).

5. The photosensitive resin composition of claim 3, wherein the alkali-soluble resin binder (A) is a polymer having organic acid groups.

6. The photosensitive resin composition of claim 3, wherein the crosslinkable compound (B) is selected from the group consisting of: compounds prepared by esterifying at least one polyhydric alcohol selected from ethylene glycol di(meth)acrylate, polyethylene glycol di(meth)acrylate having 2 to 14 ethylene groups, trimethylolpropane di(meth)acrylate, trimethylolpropane tri(meth)acrylate, pentaerythritol tri(meth)acrylate, pentaerythritol tetra(meth)acrylate, 2-trisacryloyloxymethylethylphthalic acid, propylene glycol di(meth)acrylate having 2 to propylene groups, dipentaerythritol penta(meth)acrylate, dipentaerythritol hexa(meth)acrylate and mixtures of an acid-modified product of dipentaerythritol penta(meth)acrylate and dipentaerythritol hexa(meth)acrylate, with an α,β-unsaturated carboxylic acid; compounds prepared by adding (meth)acrylic acid to at least one glycidyl group-containing compound selected from trimethylolpropane triglycidyl ether acrylic acid adducts and bisphenol A diglycidyl ether acrylic acid adducts; adducts of at least one compound having a hydroxyl group or an ethylenically unsaturated bond selected from phthalic acid diester of β-hydroxyethyl(meth)acrylate and toluene diisocyanate adducts of β-hydroxyethyl(meth)acrylate, and at least one ester selected from ester compounds of polyvalent carboxylic acids and polyisocyanate; and mixtures thereof.

7. The photosensitive resin composition of claim 3, wherein the solvent (D) is selected from the group consisting of methyl ethyl ketone, methyl cellosolve, ethyl cellosolve, ethylene glycol dimethyl ether, ethylene glycol diethyl ether, propylene glycol dimethyl ether, propylene glycol diethyl ether, diethylene glycol dimethyl ether, diethylene glycol diethyl ether, diethylene glycol methyl ethyl ether, 2-ethoxy propanol, 2-methoxy propanol, 3-methoxy butanol, cyclohexanone, cyclopentanone, propylene glycol methyl ether acetate, propylene glycol ethyl ether acetate, 3-methoxybutyl acetate, ethyl 3-ethoxypropionate, ethyl cellosolve acetate, methyl cellosolve acetate, butyl acetate, dipropylene glycol monomethyl ether, and mixtures thereof.

8. The photosensitive resin composition of claim 3, further comprising at least one additive selected from colorants, curing accelerators, thermal polymerization inhibitors, plasticizers, adhesion promoters, fillers and surfactants.

* * * * *